US012779205B2

(12) United States Patent
Breidall et al.

(10) Patent No.: US 12,779,205 B2
(45) Date of Patent: Nov. 3, 2026

(54) REDUCED THROMBOSIS BLOOD PUMP

(71) Applicant: Boston Scientific Scimed Inc, Maple Grove, MN (US)

(72) Inventors: Benjamin Breidall, Eden Prairie, MN (US); Daniel H. VanCamp, Elk River, MN (US); Travis J. Schauer, Rockford, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 865 days.

(21) Appl. No.: 18/095,732

(22) Filed: Jan. 11, 2023

(65) Prior Publication Data

US 2023/0158289 A1 May 25, 2023

Related U.S. Application Data

(63) Continuation of application No. 17/061,835, filed on Oct. 2, 2020, now Pat. No. 11,577,067.

(60) Provisional application No. 62/910,108, filed on Oct. 3, 2019.

(51) Int. Cl.
*A61M 60/825* (2021.01)
*A61M 60/419* (2021.01)
*A61M 60/818* (2021.01)

(52) U.S. Cl.
CPC ........ *A61M 60/818* (2021.01); *A61M 60/419* (2021.01)

(58) Field of Classification Search
CPC ... A61M 60/13; A61M 60/825; A61M 60/818
See application file for complete search history.

(56) References Cited

U.S. PATENT DOCUMENTS

| | | | |
|---|---|---|---|
| 931,069 | A | 8/1909 | Larrabee |
| 4,072,446 | A | 2/1978 | Walker |
| 4,265,498 | A | 5/1981 | Luce et al. |
| 4,597,678 | A | 7/1986 | Angelbeck et al. |
| 5,360,317 | A | 11/1994 | Clausen et al. |
| 5,376,114 | A | 12/1994 | Jarvik |
| 5,399,074 | A | 3/1995 | Nose et al. |
| 5,707,218 | A | 1/1998 | Maher et al. |
| 5,851,174 | A | 12/1998 | Jarvik et al. |

(Continued)

FOREIGN PATENT DOCUMENTS

| | | | |
|---|---|---|---|
| EP | 3300750 | A1 | 4/2018 |
| JP | 08-504621 | A | 5/1996 |
| WO | 98/11347 | A1 | 3/1998 |

OTHER PUBLICATIONS

International Search Report and Written Opinion received for PCT Patent Application No. PCT/US2020/053935, mailed on Jan. 29, 2021, 28 pages (13 pages of English Translation and 15 pages of Original Document).

*Primary Examiner* — Michael J D'Abreu
(74) *Attorney, Agent, or Firm* — Seager, Tufte & Wickhem LLP

(57) ABSTRACT

A bearing assembly is configured to retain a distal end of an impeller of a blood pump, where the impeller includes a drive shaft. The bearing assembly includes a pivot member coupled to a distal end of the drive shaft; a distal bearing cup having a proximally-facing surface configured to engage at least a portion of a distal section of the pivot member; and a sleeve bearing disposed around at least a portion of a proximal section of the pivot member.

12 Claims, 4 Drawing Sheets

(56) References Cited

U.S. PATENT DOCUMENTS

| | | | | |
|---|---|---|---|---|
| 5,951,263 | A | 9/1999 | Taylor et al. | |
| 5,957,672 | A | 9/1999 | Aber | |
| 6,186,665 | B1 | 2/2001 | Maher et al. | |
| 11,577,067 | B2 | 2/2023 | Breidall et al. | |
| 2014/0275722 | A1 | 9/2014 | Zimmermann et al. | |
| 2015/0159666 | A1 | 6/2015 | Mcmanus et al. | |
| 2015/0209498 | A1 | 7/2015 | Loree et al. | |
| 2019/0348888 | A1 | 11/2019 | Horng | |
| 2020/0121835 | A1 | 4/2020 | Farago et al. | |
| 2020/0197585 | A1* | 6/2020 | Scheckel ............. | A61M 60/825 |
| 2021/0100940 | A1 | 4/2021 | VanCamp | |

* cited by examiner

REDUCED THROMBOSIS BLOOD PUMP

CROSS REFERENCE TO RELATED APPLICATION

This application is a continuation of prior U.S. application Ser. No. 17/061,835, filed Oct. 2, 2020, which claims priority to Provisional Application No. 62/910,108, filed Oct. 3, 2019, which are herein incorporated by reference in their entireties.

TECHNICAL FIELD

The present disclosure relates to circulatory support devices. More specifically, the disclosure relates to bearings using in circulatory support devices.

BACKGROUND

Circulatory support devices such as blood pumps provide circulatory support. Stagnant blood areas in and around bearings, particularly due to gaps between components of the blood pump, are prone to thrombus formation.

SUMMARY

In an Example 1, a bearing assembly configured to retain a distal end of an impeller of a blood pump, the impeller having a drive shaft, and the bearing assembly comprising: a pivot member coupled to a distal end of the drive shaft; a distal bearing cup having a proximally-facing surface configured to engage at least a portion of a distal section of the pivot member; and a sleeve bearing disposed around at least a portion of a proximal section of the pivot member.

In an Example 2, the bearing assembly of Example 1, wherein the sleeve bearing is disposed between an outside surface of the proximal section of the pivot member and an inside surface of the impeller.

In an Example 3, the bearing assembly of either of Examples 1 or 2, wherein the impeller is fixed to the drive shaft and configured to rotate with the drive shaft around the sleeve bearing.

In an Example 4, the bearing assembly of any of Examples 1-3, further comprising a silicone dampener disposed around an additional portion of the proximal section of the pivot member.

In an Example 5, the bearing assembly of Example 4, wherein the proximal section of the pivot member comprises a cylindrical surface extending from a proximal end of the pivot member to a distal end of the proximal section of the pivot member, and wherein the distal section of the pivot member comprises a first surface facing in a proximal direction and oriented at least approximately perpendicular to the cylindrical surface and a second surface facing at least partially in a distal direction and curved to correspond to a curvature of the distal bearing cup.

In an Example 6, the bearing assembly of Example 5, wherein the silicone dampener comprises: a proximal section having a cylindrical inner surface configured to engage a portion of the cylindrical surface of the pivot member; and a distal section having a distally-facing inner surface configured to engage the first surface of the distal section of the pivot member.

In an Example 7, the bearing assembly of Example 6, wherein the distal section of the silicone dampener comprises a proximally-facing outer surface configured to engage a distal edge of the impeller.

In an Example 8, the bearing assembly of any of Examples 1-7, wherein the portion of the distal section of the pivot member configured to be engaged by the proximally-facing surface of the distal bearing cup is configured to engage the entire proximally-facing surface of the distal bearing cup.

In an Example 9, a blood pump, comprising: an impeller; a drive shaft disposed at least partially within the impeller; a motor configured to drive the impeller; and a distal bearing assembly disposed adjacent the motor and configured to receive a distal end of the impeller, the distal bearing assembly comprising: a pivot member coupled to a distal end of the drive shaft; a distal bearing cup having a proximally-facing surface configured to engage at least a portion of a distal section of the pivot member; and a sleeve bearing disposed around at least a portion of a proximal section of the pivot member.

In an Example 10, the blood pump of Example 9, further comprising: a proximal bearing assembly configured to retain a proximal end of the impeller of the blood pump, the proximal bearing assembly comprising: a thrust plate having a distal-facing surface; and an impeller bearing surface configured to engage the entire distal-facing surface; and a rotor fixed to the proximal end of the impeller, wherein the motor is configured to magnetically drive the rotor, the rotor comprising a cylindrical magnetic rotor having an outer surface that is located a first radial distance from a central axis of the drive shaft, and wherein the impeller bearing surface extends to a second radial distance away from the central axis, wherein the second radial distance is greater than or equal to the first radial distance.

In an Example 11, the blood pump of either of Examples 9 or 10, wherein the sleeve bearing is disposed between an outside surface of the proximal section of the pivot member and an inside surface of the impeller, and wherein the impeller is fixed to the drive shaft and configured to rotate with the drive shaft around the sleeve bearing.

In an Example 12, the blood pump of any of Examples 9-11, the distal bearing assembly further comprising a silicone dampener disposed around an additional portion of the proximal section of the pivot member.

In an Example 13, the blood pump of Example 12, wherein the proximal section of the pivot member comprises a cylindrical surface extending from a proximal end of the pivot member to a distal end of the proximal section of the pivot member, and wherein the distal section of the pivot member comprises a first surface facing in a proximal direction and oriented at least approximately perpendicular to the cylindrical surface and a second surface facing at least partially in a distal direction and curved to correspond to a curvature of the distal bearing cup.

In an Example 14, the blood pump of Example 13, wherein the silicone dampener comprises: a proximal section having a cylindrical inner surface configured to engage a portion of the cylindrical surface of the pivot member; and a distal section having a distally-facing inner surface configured to engage the first surface of the distal section of the pivot member and a proximally-facing outer surface configured to engage a distal edge of the impeller.

In an Example 15, the blood pump of any of Examples 9-14, wherein the portion of the distal section of the pivot member configured to be engaged by the proximally-facing surface of the distal bearing cup is configured to engage the entire proximally-facing surface of the distal bearing cup.

In an Example 16, a bearing assembly configured to retain a distal end of an impeller of a blood pump, the impeller having a drive shaft, and the bearing assembly comprising: a pivot member coupled to a distal end of the drive shaft; a distal bearing cup having a proximally-facing surface configured to engage at least a portion of a distal section of the pivot member; and a sleeve bearing disposed around at least a portion of a proximal section of the pivot member.

In an Example 17, the bearing assembly of Example 17, wherein the sleeve bearing is disposed between an outside surface of the proximal section of the pivot member and an inside surface of the impeller.

In an Example 18, the bearing assembly of Example 16, wherein the impeller is fixed to the drive shaft and configured to rotate with the drive shaft around the sleeve bearing.

In an Example 19, the bearing assembly of Example 16, further comprising a silicone dampener disposed around an additional portion of the proximal section of the pivot member.

In an Example 20, the bearing assembly of Example 19, wherein the proximal section of the pivot member comprises a cylindrical surface extending from a proximal end of the pivot member to a distal end of the proximal section of the pivot member, and wherein the distal section of the pivot member comprises a first surface facing in a proximal direction and oriented at least approximately perpendicular to the cylindrical surface and a second surface facing at least partially in a distal direction and curved to correspond to a curvature of the distal bearing cup.

In an Example 21, the bearing assembly of Example 20, wherein the silicone dampener comprises: a proximal section having a cylindrical inner surface configured to engage a portion of the cylindrical surface of the pivot member; and a distal section having a distally-facing inner surface configured to engage the first surface of the distal section of the pivot member.

In an Example 22, the bearing assembly of Example 21, wherein the distal section of the silicone dampener comprises a proximally-facing outer surface configured to engage a distal edge of the impeller.

In an Example 23, the bearing assembly of Example 16, wherein the portion of the distal section of the pivot member configured to be engaged by the proximally-facing surface of the distal bearing cup is configured to engage the entire proximally-facing surface of the distal bearing cup.

In an Example 24, a blood pump, comprising: an impeller; a drive shaft disposed at least partially within the impeller; a motor configured to drive the impeller; and a distal bearing assembly disposed adjacent the motor and configured to receive a distal end of the impeller, the distal bearing assembly comprising: a pivot member coupled to a distal end of the drive shaft; a distal bearing cup having a proximally-facing surface configured to engage at least a portion of a distal section of the pivot member; and a sleeve bearing disposed around at least a portion of a proximal section of the pivot member.

In an Example 25, the blood pump of Example 24, further comprising: a proximal bearing assembly configured to retain a proximal end of the impeller of the blood pump, the proximal bearing assembly comprising: a thrust plate having a distal-facing surface; and an impeller bearing surface configured to engage the entire distal-facing surface; and a rotor fixed to the proximal end of the impeller, wherein the motor is configured to magnetically drive the rotor, the rotor comprising a cylindrical magnetic rotor having an outer surface that is located a first radial distance from a central axis of the drive shaft, and wherein the impeller bearing surface extends to a second radial distance away from the central axis, wherein the second radial distance is greater than or equal to the first radial distance.

In an Example 26, the blood pump of Example 24, wherein the sleeve bearing is disposed between an outside surface of the proximal section of the pivot member and an inside surface of the impeller.

In an Example 27, the blood pump of Example 24, wherein the impeller is fixed to the drive shaft and configured to rotate with the drive shaft around the sleeve bearing.

In an Example 28, the blood pump of Example 24, the distal bearing assembly further comprising a silicone dampener disposed around an additional portion of the proximal section of the pivot member.

In an Example 29, the blood pump of Example 28, wherein the proximal section of the pivot member comprises a cylindrical surface extending from a proximal end of the pivot member to a distal end of the proximal section of the pivot member, and wherein the distal section of the pivot member comprises a first surface facing in a proximal direction and oriented at least approximately perpendicular to the cylindrical surface and a second surface facing at least partially in a distal direction and curved to correspond to a curvature of the distal bearing cup.

In an Example 30, the blood pump of Example 29, wherein the silicone dampener comprises: a proximal section having a cylindrical inner surface configured to engage a portion of the cylindrical surface of the pivot member; and a distal section having a distally-facing inner surface configured to engage the first surface of the distal section of the pivot member.

In an Example 31, the blood pump of Example 30, wherein the distal section of the silicone dampener comprises a proximally-facing outer surface configured to engage a distal edge of the impeller.

In an Example 32, the blood pump of Example 24, wherein the portion of the distal section of the pivot member configured to be engaged by the proximally-facing surface of the distal bearing cup is configured to engage the entire proximally-facing surface of the distal bearing cup.

In an Example 33, a blood pump, comprising: an impeller; a drive shaft disposed at least partially within the impeller; a rotor fixed to a proximal end of the impeller, the rotor comprising a cylindrical magnetic rotor having an outer surface that is located a first radial distance from a central axis of the drive shaft; a motor configured to drive the impeller, wherein the motor comprises a stator configured to magnetically drive the rotor; a distal bearing assembly disposed adjacent the motor and configured to receive a distal end of the impeller, the distal bearing assembly comprising: a pivot member coupled to a distal end of the drive shaft; a distal bearing cup having a proximally-facing surface configured to engage at least a portion of a distal section of the pivot member; and a sleeve bearing disposed around at least a portion of a proximal section of the pivot member; and a proximal bearing assembly configured to retain a proximal end of the impeller of the blood pump, the proximal bearing assembly comprising: a thrust plate having a distally-facing surface; and an impeller bearing surface configured to engage the entire distally-facing surface, wherein the impeller bearing surface extends to a second radial distance away from the central axis of the drive shaft, wherein the second radial distance is greater than or equal to the first radial distance.

In an Example 34, the blood pump of Example 33, further comprising a silicone dampener disposed around an additional portion of the proximal section of the pivot member.

In an Example 35, the blood pump of Example 33, wherein the portion of the distal section of the pivot member configured to be engaged by the proximally-facing surface of the distal bearing cup is configured to engage the entire proximally-facing surface of the distal bearing cup.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

Figure 1:
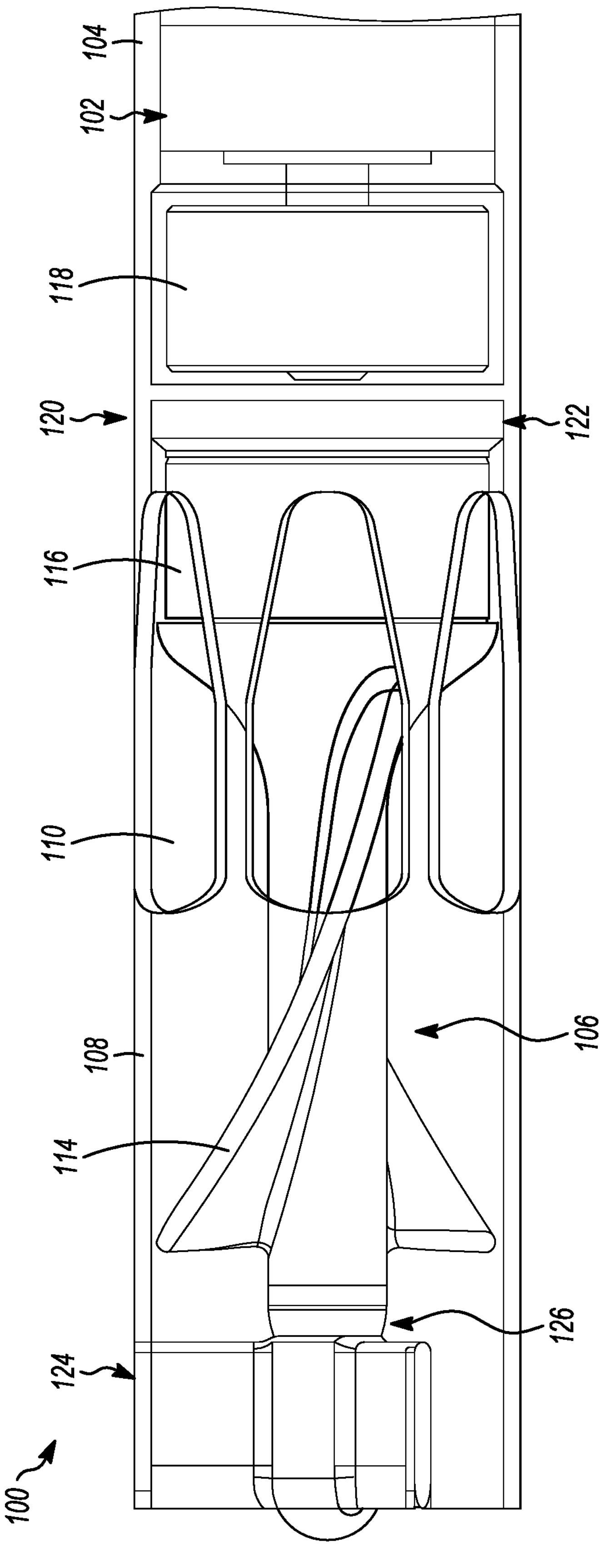
FIG. 1 depicts a partially transparent side view of a portion of an illustrative mechanical circulatory support device (also referred to herein, interchangeably, as a "blood pump"), in accordance with embodiments of the subject matter disclosed herein.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended claims.

As used herein in association with values (e.g., terms of magnitude, measurement, and/or other degrees of qualitative and/or quantitative observations that are used herein with respect to characteristics (e.g., dimensions, measurements, attributes, components, etc.) and/or ranges thereof, of tangible things (e.g., products, inventory, etc.), "about" and "approximately" may be used, interchangeably, to refer to a value, configuration, orientation, and/or other characteristic that is equal to (or the same as) the stated value, configuration, orientation, and/or other characteristic or equal to (or the same as) a value, configuration, orientation, and/or other characteristic that is reasonably close to the stated value, configuration, orientation, and/or other characteristic, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

DETAILED DESCRIPTION

Stagnant blood areas in and around bearings, particularly due to gaps between components of the blood pump, are prone to thrombus formation. Embodiments of the subject matter disclosed herein facilitate minimizing and/or eliminating these gaps and stagnant areas altogether so as to minimize the potential of thrombus formation. Existing bearing designs aim to minimize part size and complexity and utilize a more standard bearing geometry and size. Increasing the size of bearing components fills these gaps/areas and eliminates areas of blood stagnation and promotes streamlined flow through the pump. Use of high temperature materials in the bearing design can tolerate larger geometry and increased heat generation. In embodiments, a first distal bearing sleeve keeps the bearing shaft aligned with the pump components, while a second distal bearing sleeve made of silicone acts as both a dampener and a sealing mechanism to prevent blood from entering the bearing chamber. As the terms "proximal" and "distal" are used herein, "proximal" refers to the general direction opposite that of insertion—that is, the direction in which one would travel along the device to exit the subject's body; whereas distal refers to the general direction of implantation—that is, the direction in which one would travel along the device to reach the end of the device that is configured to advance into the subject's body.

Figure 2:
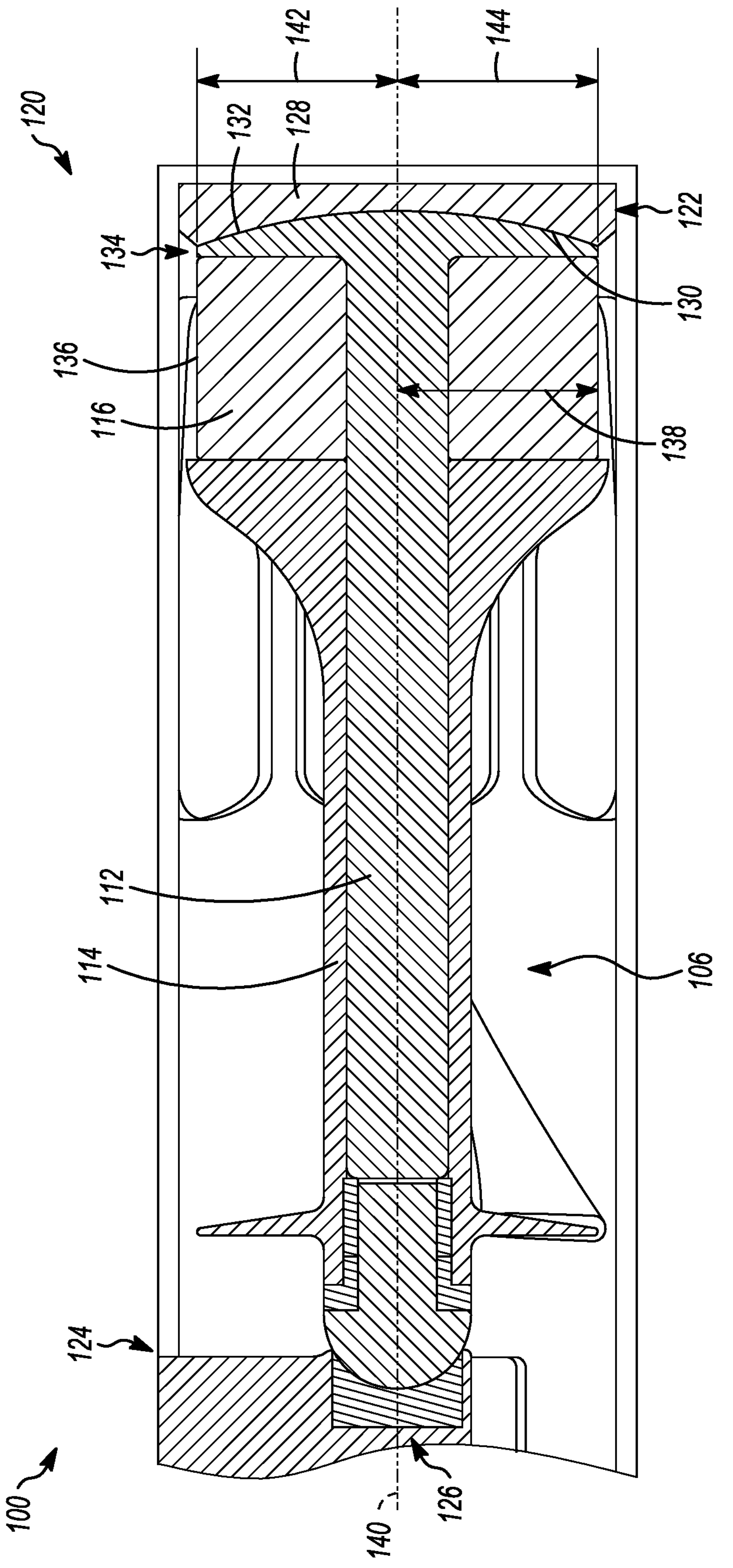
FIG. 2 depicts a cross-sectional side view of the circulatory support device depicted in FIG. 1, in accordance with embodiments of the subject matter disclosed herein.
Figure 3:
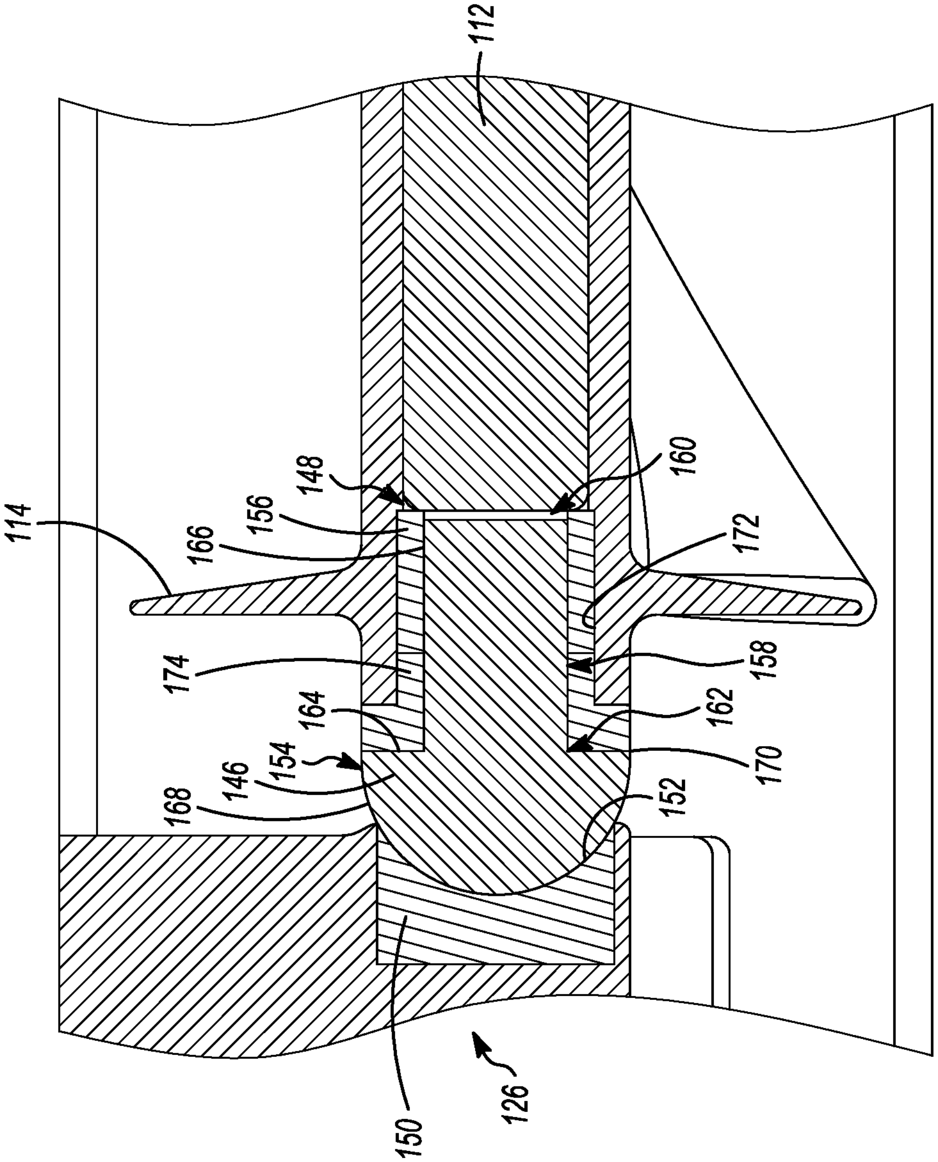
FIGS. 3 and 4 depict enlarged views of a portion of the cross-sectional side view of the circulatory support device depicted in FIG. 2, in accordance with embodiments of the subject matter disclosed herein.

FIG. 1 depicts a partially transparent view of a portion of an illustrative percutaneous mechanical circulatory support device 100 (also referred to herein, interchangeably, as a "blood pump"), in which the impeller assembly housing 108 is shown as transparent; FIG. 2 depicts a cross-sectional side view of the circulatory support device 100 depicted in FIG. 1; and FIG. 3 is an enlarged view of a portion of the cross-sectional side view of the circulatory support device 100 depicted in FIG. 2, in accordance with embodiments of the subject matter disclosed herein. As shown in FIGS. 1 and 2, the circulatory support device 100 includes a motor 102 disposed within a motor housing 104. The motor 102 is configured to drive an impeller assembly 106 to provide a flow of blood through the device 100. The impeller assembly 106 is disposed within an impeller assembly housing 108, which includes a number of outlet apertures 110 defined therein. According to embodiments, the motor housing 104 and the impeller assembly housing 108 may be integrated with one another. In other embodiments, the motor housing 104 and the impeller assembly housing 108 may be separate components configured to be coupled together, either removeably or permanently.

A controller (not shown) is operably coupled to the motor 102 and is configured to control the motor 102. The controller may be disposed within the motor housing 104 in embodiments, or, in other embodiments, may be disposed outside the housing 104 (e.g., in a catheter handle, independent housing, etc.). In embodiments, the controller may include multiple components, one or more of which may be disposed within the housing 104. According to embodiments, the controller may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. Although the controller is referred to herein in the singular, the controller may be implemented in multiple instances, distributed across multiple computing devices, instantiated within multiple virtual machines, and/or the like.

As shown in FIG. 2, the impeller assembly 106 includes a drive shaft 112 and an impeller 114 coupled thereto, where the drive shaft 112 is configured to rotate with the impeller 114. As shown, the drive shaft 112 is at least partially disposed within the impeller 114. In embodiments, the drive shaft 112 may be made of any number of different rigid materials such as, for example, steel, titanium alloys, cobalt chromium alloys, nitinol, high-strength ceramics, and/or the like. The impeller assembly 106 further includes an impeller rotor 116 fixed to the proximal end 118 of the impeller 114. The impeller rotor 116 may additionally, or alternatively, be coupled to the drive shaft 112. The impeller rotor 116 may be any type of magnetic rotor capable of being driven by a stator 118 that is part of the motor 102. In this manner, as a magnetic field is applied to the impeller rotor 116 by the stator 118 in the motor 102, the rotor 116 rotates, causing the impeller 114 to rotate.

As shown in FIGS. 1 and 2, the impeller assembly 106 is maintained in its orientation by being retained, at a first, proximal end 120, by a first (proximal) bearing assembly 122 and, at a second, distal end 124, by a second (distal) bearing assembly 126. According to embodiments, the proximal bearing assembly 122 and the distal bearing assembly 126 may include different types of bearings. According to embodiments, the proximal bearing assembly 122 and/or the distal bearing assembly 126 may include lubrication, while, in other embodiments, one and/or the other may not include lubrication.

According to embodiments, the proximal bearing assembly 122 may include a thrust plate 128 having a distal-facing surface 130. The thrust plate 128 may be made of a mineral such as, for example, sapphire. The design described herein may be configured such that no gap is formed between the distal-facing surface 130 and an impeller bearing surface 132 of the impeller assembly 106. The impeller-bearing surface 132 of the impeller assembly 106 may be dome-shaped and curved to correspond to the distally-facing surface 130. The impeller-bearing surface 132 may be configured to engage the entire distally-facing surface 130. In embodiments, the impeller-bearing surface 132 may be coupled to a proximal end 134 of the drive shaft 112. In embodiments, the impeller-bearing surface 132 may include a proximal surface of a magnet cover that is configured to be disposed over at least a proximal surface of the rotor 116. In other embodiments (e.g., in direct-drive implementations), the impeller bearing surface 132 may include a proximal surface of the impeller 114, of the rotor 116, and/or the like.

As shown, the impeller bearing surface 132 is configured such that there is no gap between the proximal end 118 of the impeller assembly 106 and the thrust plate 128. That is, for example, the rotor may include a cylindrical magnetic rotor having an outer surface 136 that is located a first radial distance 138 from a central axis 140 of the drive shaft 112, and the impeller bearing surface 132 may extend to a second radial distance 142 away from the central axis 140 of the drive shaft 112, where the second radial distance 142 is greater than or equal to the first radial distance 138. Similarly, the thrust plate 128 may be configured such that the curved, distally-facing surface 130 extends to a third radial distance 144 away from the central axis 140 of the drive shaft 112, where the third radial distance 144 is greater than or equal to the second radial distance 142.

As shown in FIG. 3, the distal bearing assembly 126 includes a pivot member 146 coupled to a distal end 148 of the drive shaft 112, a distal bearing cup 150 having a proximally-facing surface 152 configured to engage at least a portion of a distal section 154 of the pivot member 146. The pivot member 146 may be, in embodiments, ceramic, and the distal bearing cup may be made of a mineral such as sapphire. A sleeve bearing 156 may be disposed around at least a portion of the proximal section 158 of the pivot member 146. As shown, for example, the proximal section 158 of the pivot member 146 may be cylindrical in shape, coupled, at a proximal end 160 to the distal end 148 of the drive shaft 112 and terminating, at a distal end 162 in the distal section 154. The distal section 154 of the pivot member 146 may be dome-shaped, having a first, proximally-facing surface 164 that extends radially with respect to the central axis 140 and is oriented at least approximately perpendicularly to an outside cylindrical surface 166 of the proximal section 158. A second, curved, surface 168 extends from an outer edge 170 of the first surface 164. The second surface 168 includes a curvature that is configured to correspond to a curvature of the proximally-facing surface 152 of the distal bearing cup 150.

Figure 4:
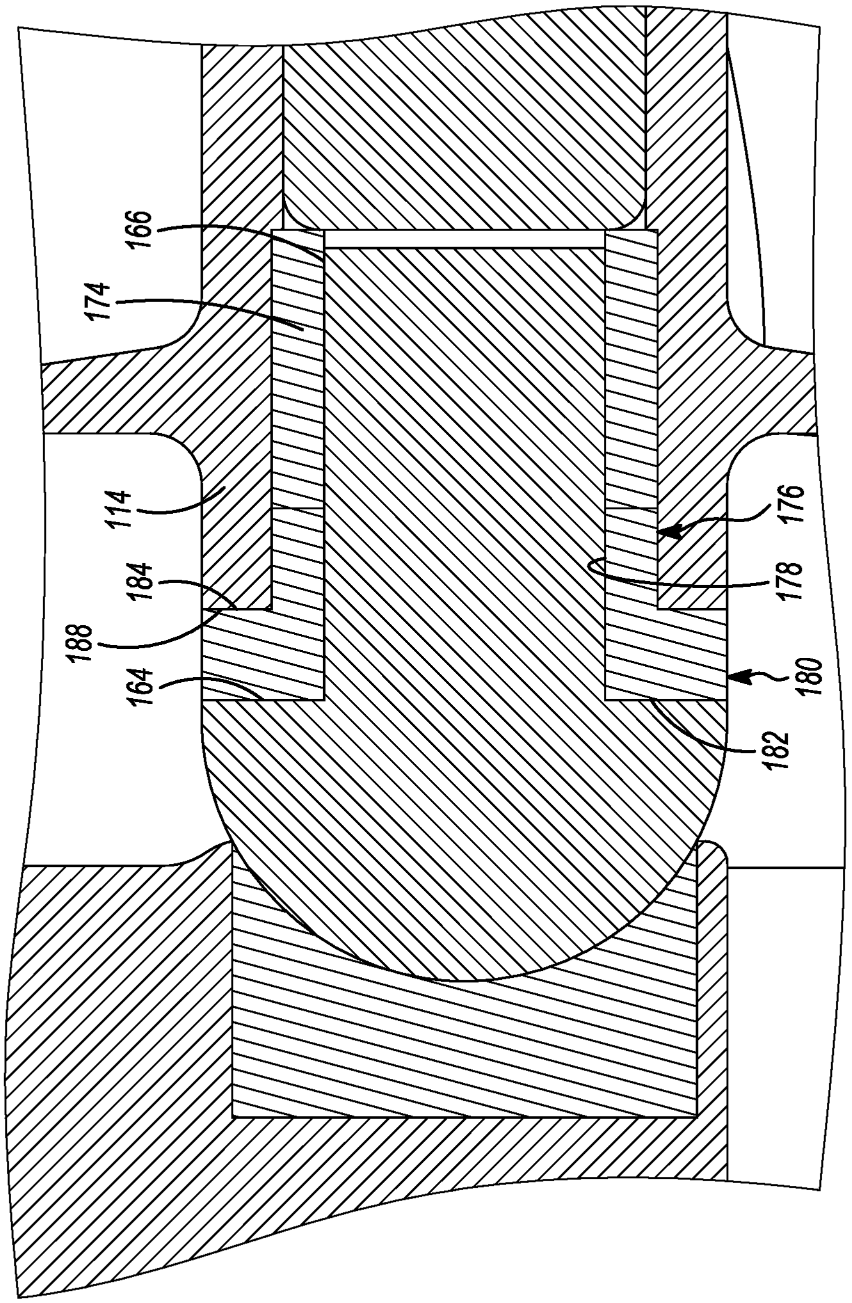

As shown, the sleeve bearing 156 is disposed between the outside surface 166 of the proximal section 158 of the pivot member 146 and an inside surface 172 of the impeller 114. The impeller 114 may be fixed to the drive shaft 112 and configured to rotate with the drive shaft 112 around the sleeve bearing 156. As is shown in FIGS. 3 and 4, the distal bearing assembly 126 further includes a silicone dampener 174 disposed around an additional portion of the proximal section 158 of the pivot member 146. According to embodiments, the silicone dampener 174 includes a proximal section 176 having a cylindrical inner surface 178 configured to engage a portion of the outside surface 166 of the proximal section 158 of the pivot member 146. The silicone dampener 174 further includes a distal section 180 having a distally-facing inner surface 182 configured to engage the first surface 164 of the distal section 154 of the pivot member 146, and a proximally-facing outer surface 184 configured to engage a distal edge 188 of the impeller 114.

According to embodiments, the silicone dampener 174 is at least partially compressible to allow some compression to maintain appropriate axial loading of the impeller assembly 106. In embodiments, the silicone dampener 174 also may be configured to function as a seal between the impeller 114 and the proximal bearing 126. In embodiments, the silicone dampener 174 is configured to be maintained in place using an interference fit, which also may facilitate ensuring that the pivot member 146 turns with the impeller 114, while the distal bearing cup 150 remains stationary.

The illustrative circulatory support device 100 shown in FIGS. 1-4 is not intended to suggest any limitation as to the scope of use or functionality of embodiments of the present disclosure. The illustrative circulatory support device 100 also should not be interpreted as having any dependency or requirement related to any single component or combination of components illustrated therein. Additionally, various components depicted in FIGS. 1-4 may be, in embodiments, integrated with various ones of the other components depicted therein (and/or components not illustrated), all of which are considered to be within the ambit of the present disclosure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A blood pump, comprising:
an impeller;
a drive shaft disposed at least partially within the impeller;
a motor configured to drive the impeller; and
a distal bearing assembly comprising:
a pivot member coupled to a distal end of the drive shaft, the pivot member comprising a proximal section and a distal section; the proximal section comprising a cylindrical surface extending from a proximal end of the pivot member to a distal end of the proximal section of the pivot member, and wherein the distal section of the pivot member comprises a first surface facing in a proximal direction and oriented at least approximately perpendicular to the cylindrical surface and a curved second surface facing at least partially in a distal direction;
a distal bearing cup having a proximally-facing surface configured to engage the curved second surface of the pivot member, the proximally-facing surface having a curvature corresponding to the curved second surface of the pivot member; and
a sleeve bearing disposed around at least a portion of the proximal section of the pivot member.

2. The blood pump of claim 1, further comprising a silicone dampener disposed around an additional portion of the proximal section of the pivot member.

3. The blood pump of claim 2, wherein the silicone dampener comprises:
a proximal section having a cylindrical inner surface configured to engage a portion of the cylindrical surface of the pivot member; and
a distal section having a distally-facing inner surface configured to engage the first surface of the distal section of the pivot member.

4. The blood pump of claim 3, wherein the distal section of the silicone dampener comprises a proximally-facing outer surface configured to engage a distal edge of the impeller.

5. The blood pump of claim 1, wherein the sleeve bearing is disposed between an outside surface of the proximal section of the pivot member and an inside surface of the impeller.

6. The blood pump of claim 1, wherein the impeller is fixed to the drive shaft and configured to rotate with the drive shaft around the sleeve bearing.

7. The blood pump of claim 1, wherein the curved second surface of the pivot member is configured to engage the entire proximally-facing surface of the distal bearing cup.

8. A blood pump, comprising:
an impeller;
a drive shaft disposed at least partially within the impeller, the drive shaft constructed of a metal;
a motor configured to drive the impeller; and
a distal bearing assembly comprising:
a pivot member coupled to a distal end of the drive shaft, the pivot member constructed of a ceramic;
a distal bearing cup having a proximally-facing surface configured to engage at least a portion of a distal section of the pivot member; and
a sleeve bearing disposed around at least a portion of a proximal section of the pivot member.

9. The blood pump of claim 8, wherein the sleeve bearing is disposed between an outside surface of the proximal section of the pivot member and an inside surface of the impeller.

10. The blood pump of claim 8, wherein the impeller is fixed to the drive shaft and configured to rotate with the drive shaft around the sleeve bearing.

11. The blood pump of claim 8, further comprising a silicone dampener disposed around an additional portion of the proximal section of the pivot member.

12. The blood pump of claim 8, wherein the proximal section of the pivot member comprises a cylindrical surface extending from a proximal end of the pivot member to a distal end of the proximal section of the pivot member, and wherein the distal section of the pivot member comprises a first surface facing in a proximal direction and oriented at least approximately perpendicular to the cylindrical surface and a second surface facing at least partially in a distal direction and curved to correspond to a curvature of the distal bearing cup.

* * * * *